US010234430B2

(12) United States Patent
Takamine

(10) Patent No.: US 10,234,430 B2
(45) Date of Patent: Mar. 19, 2019

(54) DETECTION SYSTEM, SIGNAL PROCESSING DEVICE, DETECTION METHOD, AND COMPUTER PROGRAM PRODUCT

(71) Applicant: KABUSHIKI KAISHA TOSHIBA, Tokyo (JP)

(72) Inventor: Hidefumi Takamine, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 172 days.

(21) Appl. No.: 15/255,758

(22) Filed: Sep. 2, 2016

(65) Prior Publication Data

US 2017/0074833 A1 Mar. 16, 2017

(30) Foreign Application Priority Data

Sep. 10, 2015 (JP) .................................. 2015-178552

(51) Int. Cl.
*G01N 21/88* (2006.01)
*G01N 29/04* (2006.01)
(Continued)

(52) U.S. Cl.
CPC ................ *G01N 29/14* (2013.01); *G01L 1/16* (2013.01); *G01N 21/88* (2013.01); *G01N 29/043* (2013.01);
(Continued)

(58) Field of Classification Search
CPC ...... G01N 29/14; G01N 29/043; G01N 29/38; G01N 21/88; G01N 2291/0232;
(Continued)

(56) References Cited

U.S. PATENT DOCUMENTS

| 4,592,034 A * | 5/1986 | Sachse | G01N 29/14 367/127 |
| 4,609,994 A * | 9/1986 | Bassim | G01N 29/14 702/39 |
| 6,065,342 A * | 5/2000 | Kerr | G01N 29/14 367/127 |
| 7,080,555 B2 * | 7/2006 | Austin | G01H 1/00 702/35 |

(Continued)

FOREIGN PATENT DOCUMENTS

| JP | 2-54504 | 2/1990 |
| JP | H2-242149 A | 9/1990 |

(Continued)

OTHER PUBLICATIONS

Lédeczi, Å, et al., "Wireless Acoustic Emission Sensor Network for Structural Monitoring", IEEE Sensors Journal, vol. 9, No. 11 (Nov. 2009).

*Primary Examiner* — J M Saint Surin
(74) *Attorney, Agent, or Firm* — Finnegan, Henderson, Farabow, Garrett & Dunner, L.L.P.

(57) ABSTRACT

According to an embodiment, a detection system includes a detection device, an acoustic emission sensor, and a processing unit. The detection device detects a change that occurs in a structure or a change in an environment related to the structure. The acoustic emission sensor detects an acoustic emission wave produced from the structure. The processing unit performs first signal processing to process an acoustic emission signal indicating the acoustic emission wave, which is input from the acoustic emission sensor until a first period of time elapses after a detection signal is input from the detection device. The detection signal indicates that a change has occurred in the structure or the environment related to the structure.

15 Claims, 11 Drawing Sheets

(51) Int. Cl.
*G01N 29/38* (2006.01)
*G01P 5/24* (2006.01)
*G01L 1/16* (2006.01)
*G01N 29/14* (2006.01)
*G01N 29/24* (2006.01)

(52) U.S. Cl.
CPC ......... *G01N 29/2437* (2013.01); *G01N 29/38* (2013.01); *G01P 5/24* (2013.01); *G01N 2291/0232* (2013.01); *G01N 2291/0258* (2013.01); *G01N 2291/02827* (2013.01)

(58) Field of Classification Search
CPC .. G01N 2291/0258; G01N 2291/02827; G01L 1/16; G01P 5/24
USPC .......................................................... 73/587
See application file for complete search history.

(56) References Cited

U.S. PATENT DOCUMENTS

| | | | | |
|---|---|---|---|---|
| 2002/0140566 | A1* | 10/2002 | Holroyd | G01H 1/003 340/679 |
| 2009/0326834 | A1* | 12/2009 | Sundaresan | G01M 5/0041 702/34 |
| 2012/0109582 | A1 | 5/2012 | Moriya et al. | |
| 2015/0114121 | A1* | 4/2015 | Takahashi | G01N 29/045 73/579 |
| 2015/0177195 | A1* | 6/2015 | Sasaki | G01N 29/12 73/579 |

FOREIGN PATENT DOCUMENTS

| | | |
|---|---|---|
| JP | H2-310464 A | 12/1990 |
| JP | 2003-156412 | 5/2003 |
| JP | 2006-291735 | 10/2005 |
| JP | 2010-71945 | 4/2010 |
| JP | 2011-14608 | 1/2011 |

* cited by examiner

DETECTION SYSTEM, SIGNAL PROCESSING DEVICE, DETECTION METHOD, AND COMPUTER PROGRAM PRODUCT

CROSS-REFERENCE TO RELATED APPLICATIONS

This application is based upon and claims the benefit of priority from Japanese Patent Application No. 2015-178552, filed on Sep. 10, 2015; the entire contents of which are incorporated herein by reference.

FIELD

Embodiments described herein relate generally to a detection system, a signal processing device, a detection method, and a computer program product.

BACKGROUND

When deterioration occurs in a structure such as a bridge and when load is applied to the structure, acoustic emission (AE) waves are produced from the deteriorated portion as a crack occurs and propagates. These AE waves can be detected using an AE sensor, such as a piezoelectric sensor, disposed on a surface of the structure and the number of occurrences of the AE waves can assume as an index indicating progress of the deterioration in the structure. A highly sensitive AE sensor is employed to detect the AE waves that are extremely feeble signals.

DETAILED DESCRIPTION

According to an embodiment, a detection system includes a detection device, an acoustic emission sensor, and a processing unit. The detection device detects a change that occurs in a structure or a change in an environment related to the structure. The acoustic emission sensor detects an acoustic emission wave produced from the structure. The processing unit performs first signal processing to process an acoustic emission signal indicating the acoustic emission wave, which is input from the acoustic emission sensor until a first period of time elapses after a detection signal is input from the detection device. The detection signal indicates that a change has occurred in the structure or the environment related to the structure.

An embodiment will be described in detail below with reference to the accompanying drawings.

Figure 1:
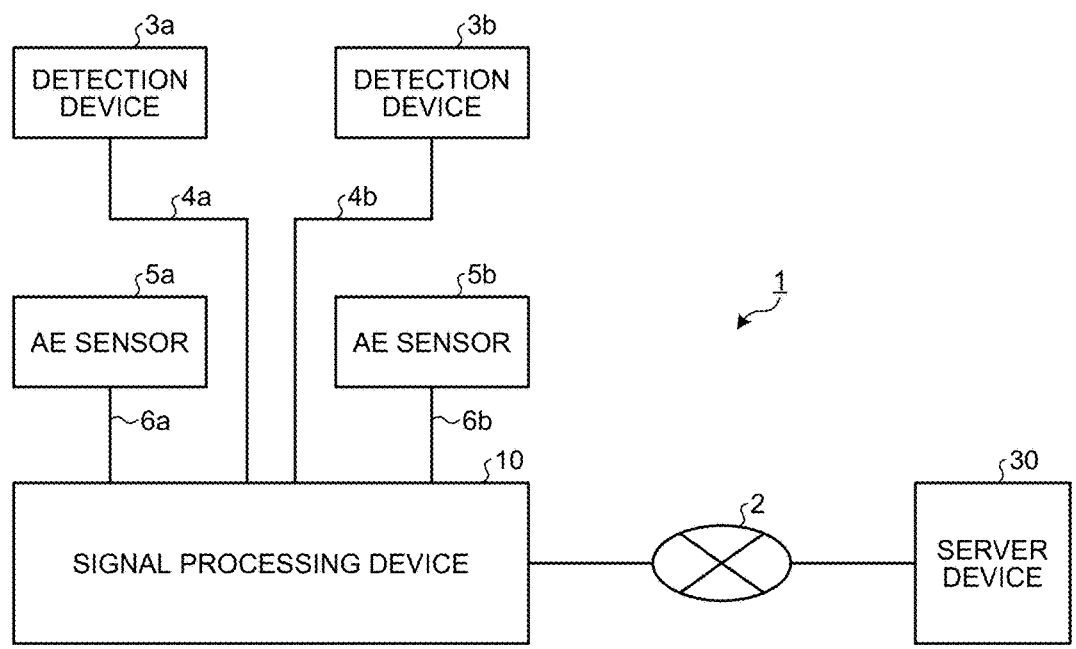
FIG. 1 is a diagram illustrating an exemplary configuration of a detection system according to an embodiment.

FIG. 1 is a diagram illustrating an exemplary configuration of a detection system 1 according to the embodiment. The detection system 1 in the embodiment includes a detection device 3a, a detection device 3b, an AE sensor 5a, an AE sensor 5b, a signal processing device 10, and a server device 30.

The detection device 3a is connected to the signal processing device 10 via a cable 4a. Similarly, the detection device 3b is connected to the signal processing device 10 via a cable 4b. The detection device 3a and the detection device 3b will hereinafter be referred to collectively as a detection device 3. Similarly, the cable 4a and the cable 4b will hereinafter be referred to collectively as a cable 4. It should be noted that the detection device 3 and the signal processing device 10 may be wirelessly connected to each other, instead of a wired connection using the cable 4; however, the wired connection is preferable considering a transmission amount between the detection device 3 and the signal processing device 10.

The AE sensor 5a is connected to the signal processing device 10 via a cable 6a. Similarly, the AE sensor 5b is connected to the signal processing device 10 via a cable 6b. The AE sensor 5a and the AE sensor 5b will hereinafter be referred to collectively as an AE sensor 5. Similarly, the cable 6a and the cable 6b will hereinafter be referred to collectively as a cable 6. It should be noted that the AE sensor 5 and the signal processing device 10 may be wirelessly connected with each other, instead of a wired connection using the cable 6; however, the wired connection is preferable considering the transmission amount between the AE sensor 5 and the signal processing device 10.

The signal processing device 10 and the server device 30 are connected to each other over a network 2. The network 2 may operate on a wireless or wired communication system, or a combination of the wireless and wired communication systems. A plurality of signal processing devices 10 may be connected with a single server device 30. Additionally, any number of detection devices 3 and AE sensors 5 may be connected to a single signal processing device 10.

The detection device 3 and the AE sensor 5 are disposed on a structure such as a bridge. When load is applied to a structure in which deterioration has occurred, the structure distorts depending on the load, a crack occurs and propagates, and AE waves are produced, for example, by propagation or friction of those cracks.

The detection device 3 detects a change in the structure or a change in an environment related to the structure. The detection device 3 in the embodiment is a strain sensor. The strain sensor detects magnitude of strain occurring in a structure and translates the strain to a corresponding detection signal indicating the magnitude of the strain. The detection signal is a voltage signal or other electric signal. The detection device 3 outputs the detection signal to the signal processing device 10.

The AE sensor 5 detects the AE waves produced from the structure and translates the AE waves to a corresponding AE signal. The AE sensor 5 may, for example, be a piezoelectric element having a sensitivity ranging between 10 kHz and 1 MHz. The AE signal is a voltage signal or other electric signal. The AE sensor 5 amplifies the AE signal and transmits the amplified AE signal to the signal processing device 10.

The signal processing device 10 performs signal processing on the AE signal transmitted from the AE sensor 5a based on the detection signal output from the detection device 3a. The signal processing device 10 also performs signal processing on the AE signal transmitted from the AE sensor 5b based on the detection signal output from the detection device 3b. The signal processing performed by the signal processing device 10 will be described later. The signal processing device 10 transmits processing result information obtained through the processing of the AE signals to the server device 30.

The server device 30, having received the processing result information from the signal processing device 10, performs processing for, for example, displaying the processing result information.

The following describes an exemplary configuration of the signal processing device.

Figure 2:
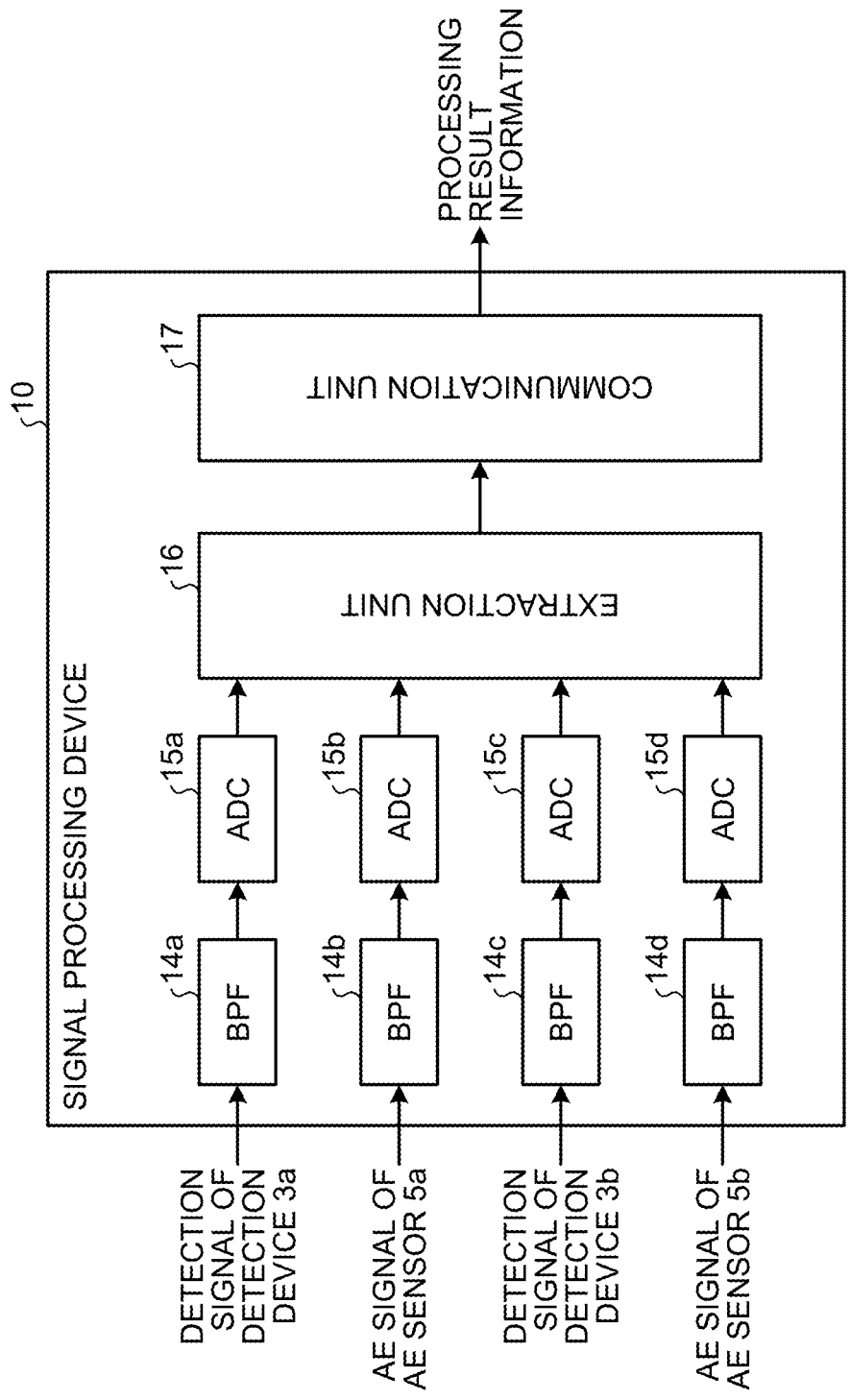
FIG. 2 is a diagram illustrating an exemplary configuration of a signal processing device according to the embodiment.

FIG. 2 is a diagram illustrating the exemplary configuration of the signal processing device 10 according to the embodiment. The signal processing device 10 in the embodiment includes band pass filters (BPFs) 14a to 14d, A/D converters (ADCs) 15a to 15d, an extraction unit 16, and a communication unit 17.

The BPFs 14a to 14d will hereinafter be referred to collectively as a BPF 14. The ADCs 15a to 15d will hereinafter be referred to collectively as an ADC 15.

The BPF 14a, having received an amplified detection signal from the detection device 3a, removes from the detection signal noise components that fall outside a predetermined frequency band. The BPF 14a outputs the noise component-removed detection signal to the ADC 15a. The ADC 15a, having received the noise component-removed detection signal from the BPF 14a, quantifies the noise component-removed detection signal and translates the quantified detection signal to a corresponding digital detection signal. The ADC 15a outputs the digital detection signal to the extraction unit 16.

Operations of the BFP14c and ADC15c are the same as the operations described for the BPF 14a and the ADC 15a and thus will not be described.

The BPF 14b, having received the amplified AE signal from the AE sensor 5a, removes from the AE signal noise components that fall outside a predetermined frequency band. The BPF 14b outputs the noise component-removed AE signal to the ADC 15b. The ADC 15b, having received the noise component-removed AE signal from the BPF 14b, quantifies the noise component-removed AE signal and translates the quantified AE signal to a corresponding digital AE signal. The ADC 15b outputs the digital AE signal to the extraction unit 16.

Operations of the BPF14d and ADC15d are the same as the operations described for the BPF 14b and the ADC 15b and thus will not be described.

The extraction unit 16 receives a detection signal of the detection device 3a from the ADC 15a. The extraction unit 16 receives an AE signal of the AE sensor 5a from the ADC 15b. The extraction unit 16 extracts, from the detection signal, characteristic parameters indicating a characteristic of the detection signal. The extraction unit 16 extracts, from the AE signal, characteristic parameters indicating a characteristic of the AE signal.

Examples of the characteristic parameters of the detection signal include, but are not limited to, amplitude [mV] of a waveform of the detection signal, duration [μsec] of the waveform of the detection signal, zero-crossing count [times] of the detection signal, energy [arb.] of the waveform of the detection signal, and frequency [Hz] of the detection signal. Similarly, examples of the characteristic parameters of the AE signal include, but are not limited to, amplitude [mV] of a waveform of the AE signal, duration [μsec] of the waveform of the AE signal, zero-crossing count [times] of the AE signal, energy [arb.] of the waveform of the AE signal, and frequency [Hz] of the AE signal.

The communication unit 17 receives the characteristic parameters of the detection signal and the characteristic parameters of the AE signal from the extraction unit 16. The communication unit 17 then transmits the characteristic parameters to the server device 30 through, for example, wireless communication. For a radio frequency band, for example, 2.4 GHz and 920 MHz bands (915 MHz to 928 MHz in Japan), what is called, the industry science medical band (ISM band) is used. It is noted that the communication unit 17 may operate on wired communication.

Communication traffic can be reduced, if the communication unit 17 transmits the detection signal and the AE signal as the characteristic parameters to the server device 30 and the server device 30 identifies the detection signal and the AE signal from the characteristic parameters, as against a case in which the communication unit 17 transmits the detection signal and the AE signal as they are. It is noted that the signal processing device 10 may transmit the detection signal and the AE signal as they are to the server device 30.

The following describes an exemplary configuration of the server device 30 in the embodiment.

Figure 3:
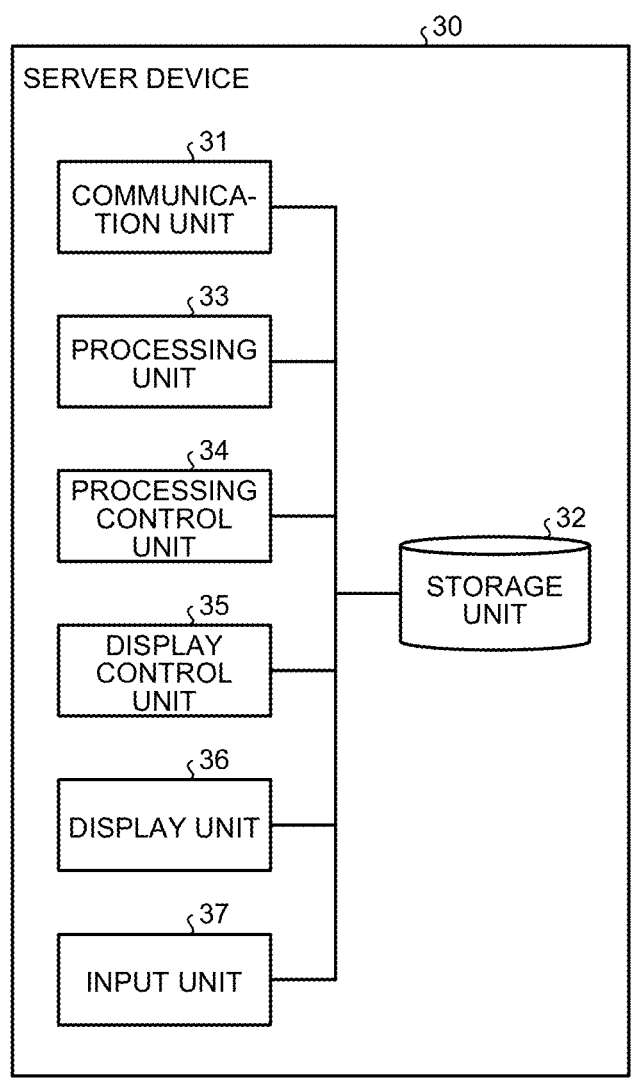
FIG. 3 is a diagram illustrating an exemplary configuration of a server device according to the embodiment.

FIG. 3 is a diagram illustrating the exemplary configuration of the server device 30. The server device 30 in the embodiment includes a communication unit 31, a storage unit 32, a processing unit 33, a processing control unit 34, a display control unit 35, a display unit 36, and an input unit 37.

The communication unit 31, having received the characteristic parameters of the detection signal and the characteristic parameters of the AE signal described above from the signal processing device 10, stores the characteristic parameters in the storage unit 32 and notifies the processing unit 33 of the characteristic parameters.

The storage unit 32 stores therein information. The storage unit 32 stores therein, for example, the characteristic parameters of the detection signal, the characteristic parameters of the AE signal, and processing result information. The processing result information represents a result of processing performed by the processing unit 33 to be described later.

The processing unit 33, having received the notification from the communication unit 31, reads the characteristic parameters of the detection signal and the characteristic parameters of the AE signal from the storage unit 32 and performs at least one signal processing of first signal processing or second signal processing. The specific signal processing performed by the processing unit 33 is determined by the processing control unit 34 to be described later.

The first signal processing is signal processing to process AE signals that are input until a first period of time elapses after the detection signal is input.

The second signal processing is signal processing to process all input AE signals.

Any type of signal processing may be performed. The signal processing include, for example, identification of waveforms of an AE signal from the characteristic parameters of the AE signal and counting of the number of waveforms that satisfy a predetermined condition, from among the waveforms of the AE signal.

The first signal processing can minimize an effect of environmental noise, compared with the second signal processing. The following describes exemplary environmental noise that affects a second signal processing result obtained from the second signal processing.

Figure 4A:
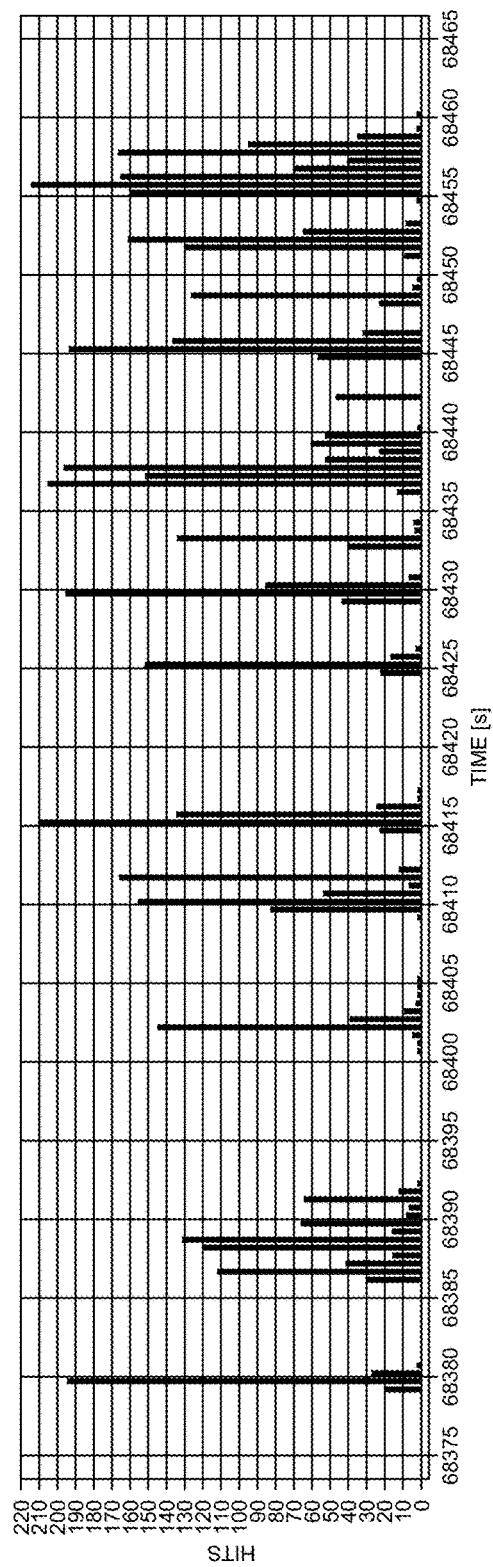
FIG. 4A is a graph exemplarily depicting AE hit counts when an effect of environmental noise is small.

FIG. 4A is a graph exemplarily depicting AE hit counts when the effect of the environmental noise is small. The graph in FIG. 4A depicts the number of waveforms (AE hit count) obtained through counting by the processing unit 33 of the waveforms satisfying a predetermined condition of the AE signals of the AE sensor 5a and the AE sensor 5b for every 0.5 seconds.

Figure 4B:
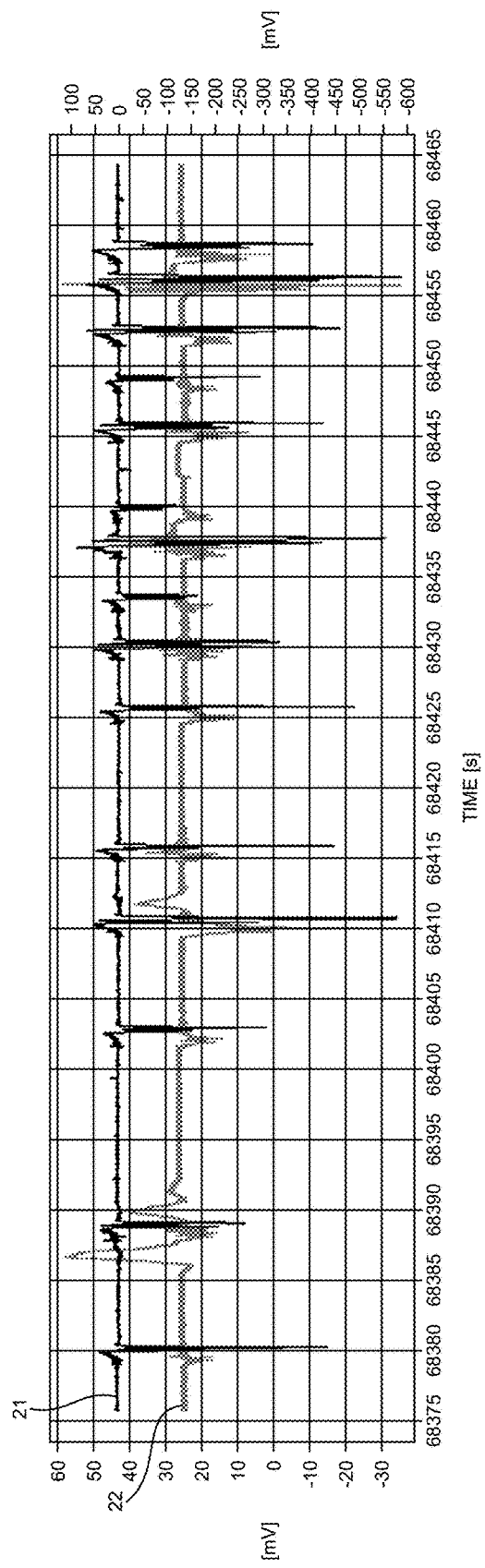
FIG. 4B depicts detection signals when the AE hit counts of FIG. 4A are calculated.

FIG. 4B depicts detection signals when the AE hit counts of FIG. 4A are calculated. A graph 21 of FIG. 4B represents the detection signal of the detection device 3a. The scale on the right indicates magnitude of voltage of the detection signal of the detection device 3a. A graph 22 of FIG. 4B represents the detection signal of the detection device 3b. The scale on the left indicates magnitude of voltage of the detection signal of the detection device 3b.

The AE hit counts of FIG. 4A are calculated from the AE signals received from the AE sensors 5a and 5b disposed on a lower surface of a sample that simulates a floor slab of the bridge. The detection signals of FIG. 4B represent signals indicating magnitude of strain received from the detection devices 3a and 3b disposed near the AE sensors 5a and 5b.

The detection device 3a is disposed, with respect to the AE sensor 5a, on a side which a moving object is expected to enter. The moving object is, for example, a vehicle. Specifically, the detection device 3a is disposed at a position at which the detection device 3a can detect strain occurring in the sample before the AE sensor 5a can. This arrangement enables the detection device 3a to transmit the detection signal to the signal processing device 10 before the moving object enters a zone in which the AE sensor 5a is disposed.

Similarly, the detection device 3b is disposed, with respect to the AE sensor 5b, on a side which the moving object is expected to enter. Specifically, the detection device 3b is disposed at a position at which the detection device 3b can detect strain occurring in the sample before the AE sensor 5b can. This arrangement enables the detection device 3b to transmit the detection signal to the signal processing device 10 before the moving object enters a zone in which the AE sensor 5b is disposed.

As illustrated in FIGS. 4A and 4B, when the effect of the environmental noise is small, the AE hit count occurs at timing at which the detection signal is obtained. FIGS. 4A and 4B indicate that the AE waves occurring to correspond to the load applied by the movement of the moving object are detected.

Figure 5A:
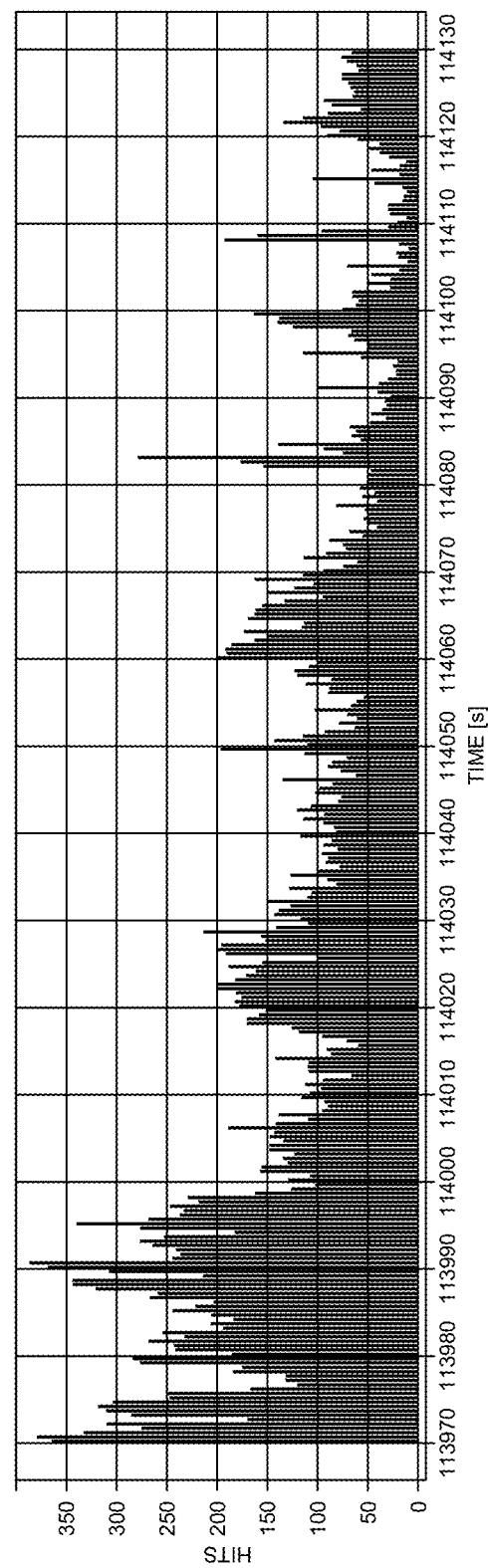
FIG. 5A is a graph exemplarily depicting AE hit counts when the effect of environmental noise is large.
Figure 5B:
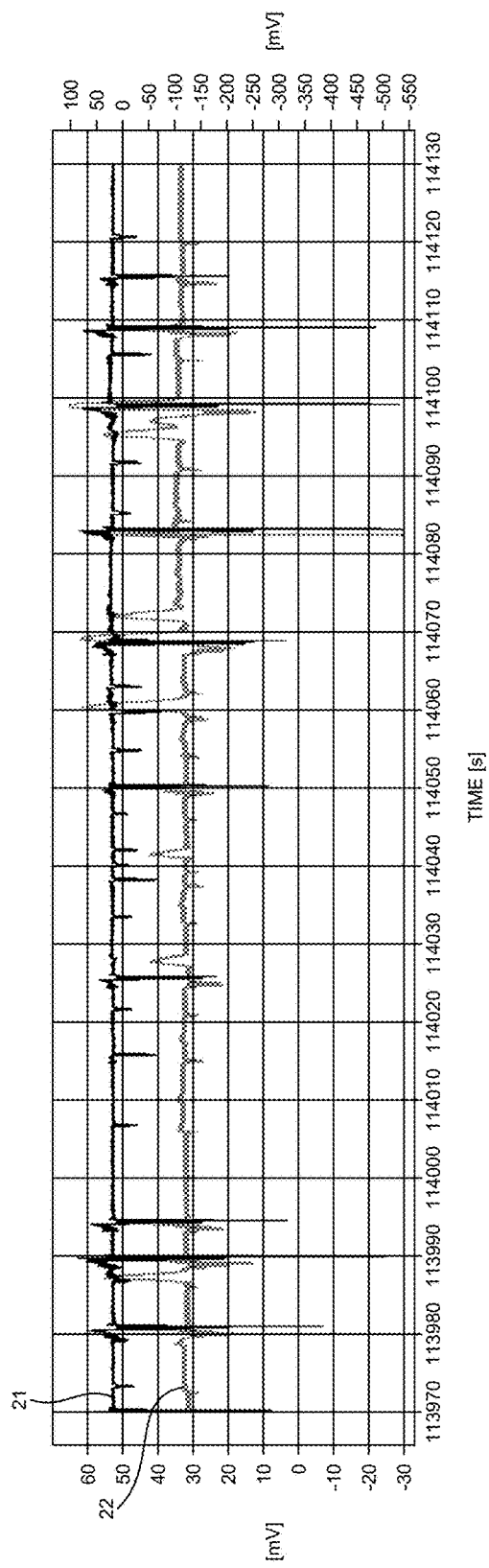
FIG. 5B depicts detection signals when the AE hit counts of FIG. 5A are calculated.

FIG. 5A is a graph exemplarily depicting AE hit counts when the effect of the environmental noise is large. FIG. 5B depicts detection signals when the AE hit counts of FIG. 5A are calculated. Descriptions for FIGS. 5A and 5B are the same as those for FIGS. 4A and 4B and are thus omitted. Descriptions for positional relations between the AE sensors 5a and 5b and the detection devices 3a and 3b are the same as those given for FIGS. 4A and 4B and thus are omitted.

FIG. 5A exemplarily depicts the AE hit counts when disturbance that simulates the environment noise is given. FIG. 5A depicts that the AE hit counts are observed at all times regardless of the timing at which the detection signal of FIG. 5B occurs. The AE hit counts depicted in FIG. 5A include a large number of AE hit counts of AE waves not arising from, for example, occurrence and propagation of a crack. Specifically, the environmental noise is counted at all times as the AE hit counts. The environmental noise represents noise components unnecessary for diagnosis of deterioration in structures.

The first signal processing performed by the processing unit 33 described previously can reduce the effect of the environmental noise, compared with the second signal processing. The following describes specifically the first signal processing.

Figure 6:
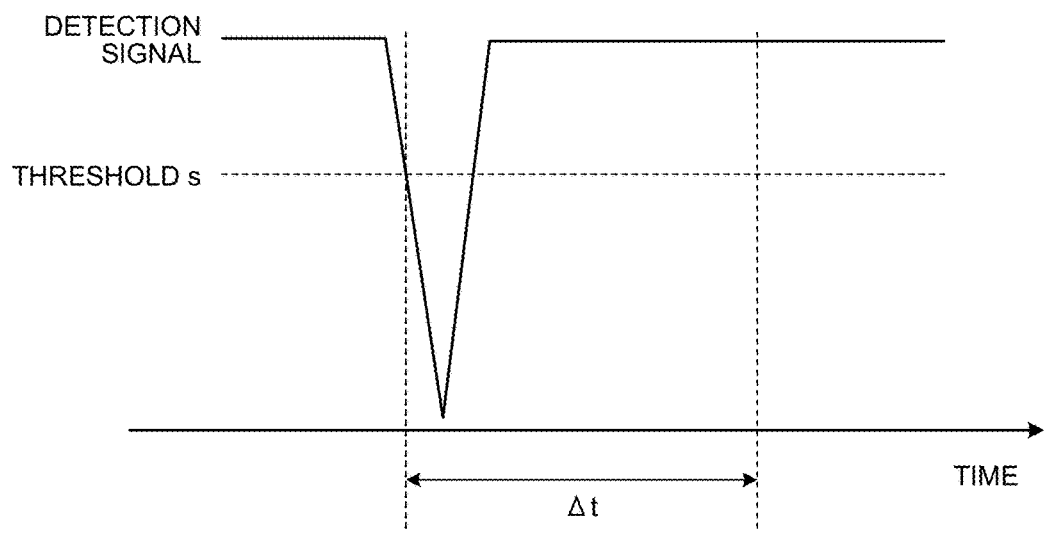
FIG. 6 is a diagram illustrating an exemplary first period of time in first signal processing in the embodiment.

FIG. 6 is a diagram illustrating an exemplary first period of time Δt in the first signal processing according to the embodiment. When the magnitude of the strain indicated by a detection signal exceeds a threshold s, the processing unit 33 performs signal processing on the AE signal, which is input to the signal processing device 10 until the first period of time Δt elapses after the detection signal is input to the signal processing device 10.

More specifically, when the magnitude of the strain indicated by the detection signal of the detection device 3a exceeds a threshold $s_1$, the processing unit 33 performs the signal processing on the AE signal, which is input from the AE sensor 5a until the first period of time Δt elapses after the detection signal is input from the detection device 3a. When the magnitude of the strain indicated by the detection signal of the detection device 3b exceeds a threshold $s_2$, the processing unit 33 performs the signal processing on the AE signal, which is input from the AE sensor 5b until the first period of time Δt elapses after the detection signal is input from the detection device 3b.

The threshold s of the detection signal is evaluated using a criterion, whether the threshold s is exceeded on a plus side or on a minus side, depending on how the detection device 3 is disposed. For example, the detection signal of one detection device 3 behaves in a reverse way depending on whether the detection device 3 is disposed at a position at which the detection device 3 is compressed or extended when load is applied to the structure.

In the example illustrated in FIG. 6, it is determined whether or not the threshold s of the detection signal is exceeded on the minus side depending on the load applied to the structure for which the AE hit count is calculated. Specifically, timing at which the magnitude of the strain indicated by the detection signal falls short of the predetermined threshold s triggers the start of counting the AE hit count. This arrangement enables the first signal processing to reduce the effect of the environmental noise, compared with the second signal processing.

Referring back to FIG. 3, the processing unit 33 stores, in the storage unit 32, processing result information that includes at least one of a first signal processing result obtained through the first signal processing and a second signal processing result obtained through the second signal processing.

The processing control unit 34 causes the processing unit 33 of the signal processing device 10 to perform at least one signal processing of the first signal processing or the second signal processing result. Specifically, the processing control unit 34 causes the processing unit 33 to perform at least one of the first signal processing and the second signal processing in accordance with, for example, setting information set by the user on, for example, a setting screen displayed on the display unit 36.

The display control unit 35 displays display information on the display unit 36. For example, the display control unit 35 reads the processing result information from the storage unit 32 and displays the display information including the processing result information on the display unit 36.

The display unit 36 displays information in accordance with the control by the display control unit 35. The input unit 37 receives an input of information corresponding to an operation by the user. The input unit 37 receives from the user, for example, setting information based on the processing result information displayed on the display unit 36. Examples of the setting information based on the processing result information include, but are not limited to, values changed for parameters, such as the threshold s and the first period of time Δt, and information indicating changeover of the signal processing method.

Figure 7:
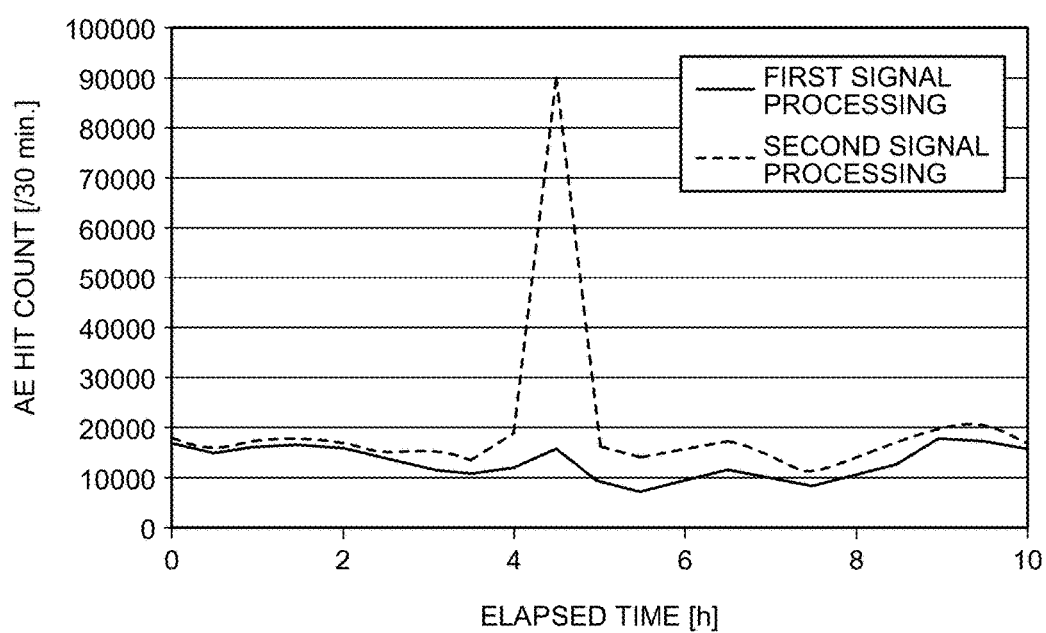
FIG. 7 is a diagram illustrating exemplary display information in the embodiment.

FIG. 7 is a diagram illustrating exemplary display information in the embodiment. In FIG. 7, the abscissa of the display information represents elapsed time (h) after the detection of the AE hit counts starts. In FIG. 7, the ordinate of the display information represents the AE hit count calculated every 30 minutes. The display information depicted in FIG. 7 includes the first signal processing result information and the second signal processing result information described above. The graph depicting the second signal processing result information indicates that the AE hit count increases considerably at timing of four to five hours after the detection of the AE hit counts starts. In contrast, the graph depicting the first signal processing result information indicates that the AE hit count increases far less at the timing of four to five hours after the detection of the AE hit counts starts than the graph depicting the second signal processing result information. This is because the first signal processing can reduce the AE hit counts arising from the environmental noise, compared with the second signal processing. Specifically, the first signal processing can reduce the effect of the environmental noise, compared with the second signal processing.

The following describes a detection method according to the embodiment.

Figure 8:
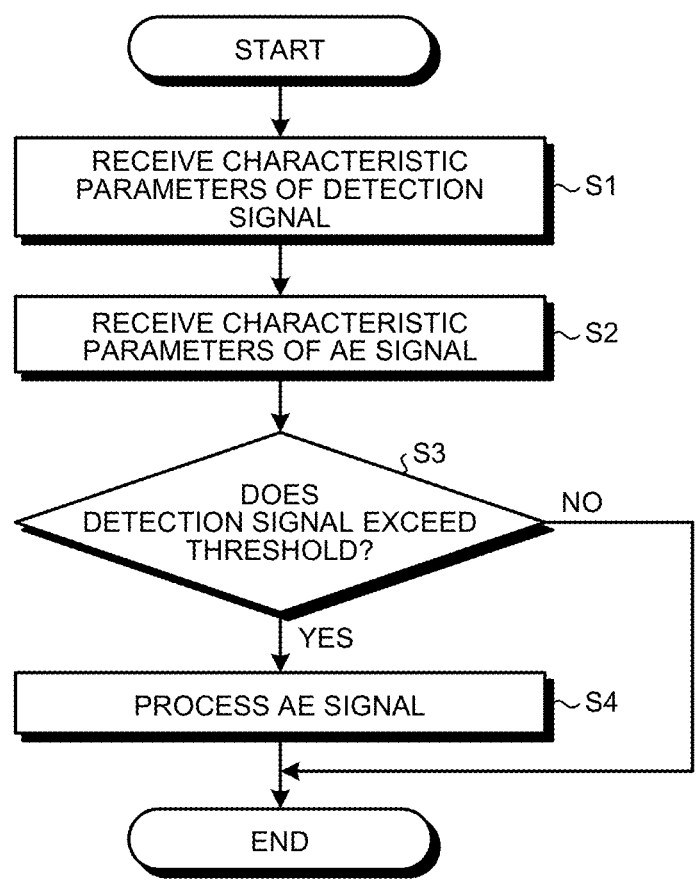
FIG. 8 is a flowchart illustrating exemplary steps of the first signal processing in the embodiment.

FIG. 8 is a flowchart illustrating exemplary steps of the first signal processing in the embodiment. The communication unit 31 receives the characteristic parameters of a detection signal from the detection device 3 (Step S1). The communication unit 31 receives the characteristic parameters of an AE signal from the AE sensor 5 (Step S2). The processing unit 33 determines whether the magnitude of the strain indicated by the detection signal exceeds the threshold s based on the characteristic parameters of the detection signal (Step S3).

If the magnitude of the strain indicated by the detection signal exceeds the threshold s (Yes at Step S3), the processing unit 33 performs, based on the characteristic parameters of the AE signal, the signal processing on the AE signal, which is input to the signal processing device 10 until the first period of time Δt elapses after the detection signal is input to the signal processing device 10 (Step S4).

If the magnitude of the strain indicated by the detection signal is equal to or smaller than the threshold s (No at Step S3), the processing unit 33 terminates the first signal processing without performing the signal processing for the AE signal received at Step S2.

As described above, in the detection system 1 in the embodiment, the detection device 3 detects strain that occurs in a structure and the AE sensor 5 detects AE waves produced from the structure. The processing unit 33 performs the first signal processing to process the AE signal, which is input to the signal processing device 10 from the AE sensor until the first period of time Δt elapses after the detection signal is input to the signal processing device 10 from the detection device 3. Thus, the detection system 1 according to the embodiment can further reduce the effect of the environment noise included in the result of signal processing.

Modification of Embodiment

The following describes a modification of the embodiment. The following omits descriptions similar to those given for the embodiment. Arrangements of a detection system 1 according to the modification of the embodiment are the same as those of the detection system 1 in the embodiment (see FIG. 1) and descriptions therefor will be omitted. Arrangements of a signal processing device 10 according to the modification of the embodiment are the same as those of the signal processing device 10 in the embodiment (see FIG. 2) and descriptions therefor will be omitted.

Timing at which the processing unit 33 starts processing the AE signal may not have to coincide with timing at which the detection signal exceeds the threshold s. Assume, for example, a configuration in which the detection device 3 is disposed at a position spaced away from the AE sensor 5. A time difference is produced between timing at which strain occurs in the detection device 3 and timing at which AE waves are produced by strain near the AE sensor 5, due to load applied to the structure such as a bridge when the moving object passes on the structure. In such a case, preferably, the distance between the detection device 3 and the AE sensor 5 is taken into consideration. Specifically, preferably, timing at which the processing unit 33 starts processing the AE signal is retarded.

In the detection system 1 according to the modification of the embodiment, the timing at which a processing unit 33 starts the above-described first signal processing differs from the corresponding timing in the detection system 1 according to the embodiment. The following describes the first signal processing performed in the modification of the embodiment.

Figure 9:
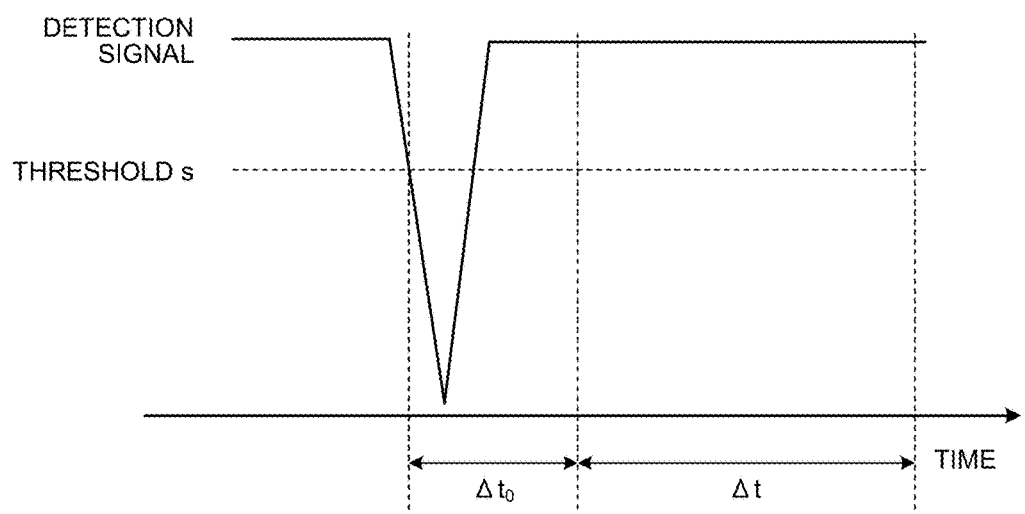
FIG. 9 is a diagram illustrating an exemplary first period of time and an exemplary second period of time in a modification of the embodiment.

FIG. 9 is a diagram illustrating an exemplary first period of time Δt and an exemplary second period of time $\Delta t_0$ in the modification of the embodiment. The processing unit 33 processes the AE signal, which is input from the AE sensor 5 to the signal processing device 10 until the first period of time Δt elapses from a time point when the second period of time $\Delta t_0$ elapses after the detection signal is input to the signal processing device 10 from a detection device 3. In a case where v is an average speed of a moving object that passes on the bridge and the detection device 3 is disposed at a position spaced a distance d away from the AE sensor 5 on the side which the moving object enters, the second period of time $\Delta t_0$ is, for example, d/v.

As described above, in the detection system 1 according to the modification of the embodiment, the processing unit 33 processes the AE signal, which is input from the AE sensor 5 to the signal processing device 10 until the first period of time Δt elapses from a time point when the second period of time $\Delta t_0$ elapses after the detection signal is input to the signal processing device 10 from the detection device 3. This arrangement enables the detection system 1 according to the modification of the embodiment to even more effectively reduce the environmental noise component included in the AE signal.

The following describes an exemplary hardware configuration of the server device 30.

Figure 10:
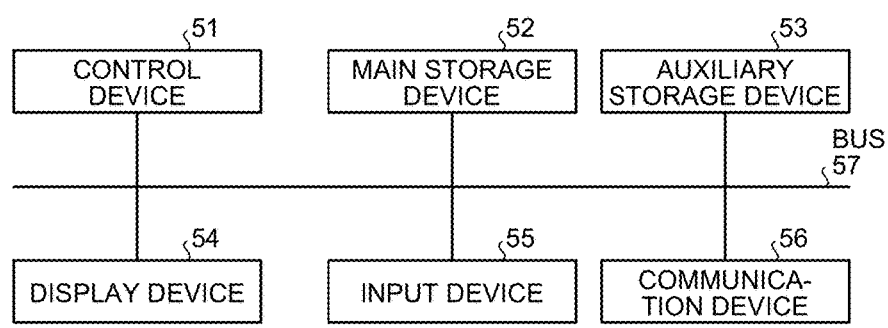
FIG. 10 is a diagram illustrating an exemplary hardware configuration of the server device according to the embodiment.

FIG. 10 is a diagram illustrating the exemplary hardware configuration of the server device 30 according to the embodiment. The server device 30 in the embodiment includes a control device 51, a main storage device 52, an auxiliary storage device 53, a display device 54, an input device 55, and a communication device 56. The control device 51, the main storage device 52, the auxiliary storage device 53, the display device 54, the input device 55, and the communication device 56 are connected to each other via a bus 57. The server device 30 may, for example, be a smart device and a personal computer.

The control device 51 executes a program loaded from the auxiliary storage device 53 to the main storage device 52. The main storage device 52 is a memory such as a ROM and a RAM. The auxiliary storage device 53 is, for example, a memory card and a solid state drive (SSD). The auxiliary storage device 53 corresponds to the storage unit 32 described previously.

The display device 54 displays information. The display device 54 corresponds to the display unit 36 described previously. The display device 54 is, for example, a liquid crystal display. The input device 55 receives an input of information. The input device 55 is, for example, a keyboard. It is noted that the display unit 54 and the input device 55 may, for example, be a liquid crystal panel having a display function and an input function. The communication device 56 communicates with other devices.

The program executed by the server device 30 is provided as a computer program product by being recorded in a computer-readable recording medium such as a compact disc read only memory (CD-ROM), a memory card, a compact disc recordable (CD-R), and a digital versatile disc (DVD), as an installable or executable file.

The program executed by the server device 30 may be stored in a computer connected to a network such as the Internet and provided by being downloaded via the network. Furthermore, the program executed by the server device 30 may be provided via a network such as the Internet without being downloaded.

The program executed by the server device 30 may even be provided by being incorporated in, for example, a ROM in advance.

The program executed by the server device 30 has a modular configuration including, out of the configuration (functional blocks) of the server device 30 of the embodiment, functional blocks that can be achieved by the program. Examples of the functional blocks that can be achieved by the program include, but are not limited to, the communication unit 31, the processing unit 33, the processing control unit 34, the display control unit 35, and the input unit 37.

Each of the functional blocks that can be achieved by the program is loaded on the main storage device 52 as a result of the control device 51 loading the program from a storage medium such as the auxiliary storage device 53 and executing the loaded program. Specifically, the functional blocks that can be achieved by the program are generated on the main storage device 52.

It is noted that the functional blocks of the server device 30 in the embodiment may even be achieved by combining the program with hardware such as an integrated circuit (IC).

While certain embodiments have been described, these embodiments have been presented by way of example only, and are not intended to limit the scope of the invention. Indeed, the novel system, device, method, and computer program described herein may be embodied in a variety of other forms; furthermore, various omissions, substitutions and changes in the form of the system, device, method, and computer program described herein may be made without departing from the spirit of the invention. The accompanying claims and their equivalents are intended to cover such forms or modifications as would fall within the scope and spirits of the invention.

For example, the detection device 3 is required only to detect a change occurring in a structure or a change in an environment related to the structure. When the structure is, for example, a bridge, the detection device 3 may be a camera that captures a moving object entering the structure. In this case, when the moving object is included in the image captured by the detection device 3, the detection device 3 inputs the detection signal to the signal processing device 10. Specifically, the processing unit 33 may perform the first signal processing of the AE signal, which is input to the signal processing device 10 until the first period of time $\Delta t$ elapses after the detection signal based on the captured image is input to the signal processing device 10.

Additionally, the AE sensor 5 may be used for the detection device 3. In this case, the AE sensor 5 used as the detection device 3 is adjusted so as to detect acoustic waves in a frequency band indicating strain in the structure.

The type of structure to be detected by the detection system 1 is not limited to bridges. Consider, for example, a building as the structure to be detected. In this case, the AE sensor 5 may be disposed in the building and the detection device 3 may, for example, be a vibration sensor that detects P-waves of earthquakes. Specifically, when a structure is subjected to vibration in an earthquake, the processing unit 33 may perform the first signal processing to process the AE signal, which is input to the signal processing device 10 until the first period of time $\Delta t$ elapses after the occurrence of the earthquake hitting the building.

If the structure is, for example, a high-rise building, the detection device 3 may, for example, be a wind velocity sensor that detects wind velocity. Specifically, when the magnitude of wind velocity indicated by the detection signal exceeds a threshold s, the processing unit 33 may perform the first signal processing to process the AE signal, which is input to the signal processing device 10 until the first period of time $\Delta t$ elapses after the detection signal is input to the signal processing device 10.

Take, for instance, a pipe through which a fluid passes as the structure to be detected and dispose the AE sensor 5 on a surface of the pipe. If deterioration of the pipe progresses due to, for example, load of pressure of the fluid flowing through the pipe, a flowmeter, for example, may be used as the detection device 3. The processing unit 33 may perform the first signal processing to process the AE signal, which is input to the signal processing device 10 until the first period of time $\Delta t$ elapses after the flowmeter disposed upstream in a flow direction detects passage of a fluid having a flow rate exceeding a threshold s.

Additionally, any device may be used to achieve each of the functional blocks described above (see FIGS. 2 and 6). For example, the processing unit 33 of the server device 30 may be achieved by the signal processing device 10. The AE sensor 5 and the signal processing device 10 may be achieved with a single housing.

The embodiment has been described for a configuration that includes the detection device 3a and the AE sensor 5a, and the detection device 3b and the AE sensor 5b. Nonetheless, any number of detection devices 3a and AE sensors 5a may be connected with the signal processing device 10.

For example, one detection device 3 and one AE sensor 5 may be connected with the signal processing device 10.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A detection system comprising:
   a detection device configured to detect a change that occurs in a structure or a change in an environment related to the structure;
   an acoustic emission sensor configured to detect an acoustic emission wave produced from the structure; and
   a processing unit configured to perform first signal processing to process an acoustic emission signal indicating the acoustic emission wave, which is input from the acoustic emission sensor until a first period of time elapses after a detection signal is input from the detection device, the detection signal indicating that a change has occurred in the structure or the environment related to the structure.

2. The system according to claim 1, wherein the detection device is disposed at a position at which the detection device detects the change that occurs in the structure before the acoustic emission sensor does.

3. The system according to claim 1, wherein the processing unit processes the acoustic emission signal input from the acoustic emission sensor until the first period of time elapses from elapse of a second period of time after the detection signal is input from the detection device.

4. The system according to claim 3, wherein
   the change that occurs in the structure includes strain of the structure arising from weight of a moving object that enters the structure, and
   the second period of time is determined based on a distance between the detection device and the acoustic emission sensor and an average speed of the moving object.

5. The system according to claim 4, wherein
   the detection device includes a camera that captures the moving object that enters the structure, and
   when the moving object is included in an image captured by the camera, the detection device inputs the detection signal to the processing unit.

6. The system according to claim 1, wherein
   the detection device is a strain sensor configured to detect magnitude of strain occurring in the structure,
   the detection signal indicates the magnitude of the strain occurring in the structure, and
   when the magnitude of the strain indicated by the detection signal exceeds a threshold, the processing unit performs the first signal processing on the acoustic emission signal, which is input from the acoustic emission sensor until the first period of time elapses after the detection signal is input from the detection device.

7. The system according to claim 6, wherein the strain sensor is an acoustic emission sensor configured to detect an acoustic wave in a frequency band indicating strain in the structure.

8. The system according to claim 1, wherein
   the detection device is a vibration sensor configured to detect magnitude of vibration occurring in the structure,
   the detection signal indicates the magnitude of the vibration occurring in the structure, and
   when the magnitude of the vibration indicated by the detection signal exceeds a threshold, the processing unit performs the first signal processing on the acoustic emission signal, which is input from the acoustic emission sensor until the first period of time elapses after the detection signal is input from the detection device.

9. The system according to claim 1, wherein
   the detection device is a wind velocity sensor configured to detect magnitude of wind velocity with respect to the structure,
   the detection signal indicates the magnitude of the wind velocity with respect to the structure, and
   when the magnitude of the wind velocity indicated by the detection signal exceeds a threshold, the processing unit performs the first signal processing on the acoustic emission signal, which is input from the acoustic emission sensor until the first period of time elapses after the detection signal is input from the detection device.

10. The system according to claim 1, wherein
    the detection device is a flowmeter configured to detect a flow rate of a fluid flowing through the structure,
    the detection signal indicates the flow rate of the fluid, and
    when the flow rate indicated by the detection signal exceeds a threshold, the processing unit performs the first signal processing on the acoustic emission signal, which is input from the acoustic emission sensor until the first period of time elapses after the detection signal is input from the detection device.

11. The system according to claim 1, further comprising:
    a processing control unit configured to cause the processing unit to perform at least one of second signal processing to process the acoustic emission signal at all times and the first signal processing; and
    a display control unit configured to display, on a display unit, at least one of first signal processing result information that indicates a processing result of the first signal processing and second signal processing result information that indicates a processing result of the second signal processing.

12. The system according to claim 11, wherein the first signal processing and the second signal processing include processing to count waveforms that satisfy a predetermined condition, from among waveforms indicated by the acoustic emission signal.

13. A signal processing device connected to a detection device and to an acoustic emission sensor, the detection device being configured to detect a change that occurs in a structure or a change in an environment related to the structure, the acoustic emission sensor being configured to detect an acoustic emission wave produced from the structure, the signal processing device comprising:
    a processing unit configured to perform first signal processing to process an acoustic emission signal indicating the acoustic emission waves, which is input from the acoustic emission sensor until a first period of time elapses after a detection signal is input from the detection device, the detection signal indicating that a change has occurred in the structure or the environment related to the structure.

14. A detection method performed by a signal processing device connected to a detection device and to an acoustic emission sensor, the detection device being configured to detect a change that occurs in a structure or a change in an environment related to the structure, the acoustic emission sensor being configured to detect an acoustic emission wave produced from the structure, the method comprising:

performing first signal processing to process an acoustic emission signal indicating the acoustic emission waves, which is input from the acoustic emission sensor until a first period of time elapses after a detection signal is input from the detection device, the detection signal indicating that a change has occurred in the structure or the environment related to the structure.

15. A computer program product comprising a non-transitory
computer-readable medium including programmed instructions, wherein the instructions causes a computer, which is connected to a detection device and to an acoustic emission sensor, the detection device being configured to detect a change that occurs in a structure or a change in an environment related to the structure, the acoustic emission sensor being configured to detect an acoustic emission wave produced from the structure, to function as:
a processing unit configured to perform first signal processing to process an acoustic emission signal indicating the acoustic emission wave, which is input from the acoustic emission sensor until a first period of time elapses after a detection signal is input from the detection device, the detection signal indicating that a change has occurred in the structure or the environment related to the structure.

* * * * *